United States Patent [19]

Speranza et al.

[11] 4,228,310

[45] Oct. 14, 1980

[54] POLYOL PREPARATION

[75] Inventors: George P. Speranza; Robert L. Zimmerman; Thomas H. Austin, all of Austin, Tex.

[73] Assignee: Texaco Development Corp., White Plains, N.Y.

[21] Appl. No.: 21,517

[22] Filed: Mar. 19, 1979

Related U.S. Application Data

[63] Continuation of Ser. No. 916,991, Jun. 19, 1978, abandoned.

[51] Int. Cl.² ............... C07C 43/11; C07C 41/02
[52] U.S. Cl. ............... 568/620; 260/584 B; 568/606; 568/611; 568/614; 568/622; 568/623; 568/624; 568/625; 568/662; 568/670; 568/676; 568/678; 568/680; 521/88; 521/155; 521/902

[58] Field of Search ............... 568/620, 606, 611, 614, 568/618, 619, 623, 624, 625, 622, 662, 670, 676, 678, 680; 260/584 B

[56] References Cited

U.S. PATENT DOCUMENTS

| | | | |
|---|---|---|---|
| 3,357,970 | 12/1967 | Wyatt et al. | 568/620 X |
| 3,745,133 | 7/1973 | Comunale et al. | 521/118 X |

*Primary Examiner*—Howard T. Mars
*Attorney, Agent, or Firm*—Carl G. Ries; Robert A. Kulason; James L. Bailey

[57] ABSTRACT

Covers a method of preparing polyether polyols useful in making a polyisocyanurate polymer by oxyalkylating an alcohol by the catalytic addition of an alkylene oxide to said alcohol in presence of a catalyst selected from the group consisting of carbamate salts, aminophenols, hexahydro-s-triazines and tetrahydrooxadiazines.

10 Claims, No Drawings

POLYOL PREPARATION

This application is a continuation-in-part of application Ser. No. 916,991 filed June 19, 1978 and now abandoned.

BACKGROUND OF THE INVENTION

1. Field of the Invention

This invention relates to the field of preparing polyether polyols. More particularly, this invention relates to the use of isocyanurate catalysts in promoting oxyalkylation of specific alcohols.

2. Description of the Prior Art

Alkylene oxide adducts of various alcohols, aminoalcohols, etc. are well known and widely used in a variety of industries. Such polyoxyalkylene polyhydric compounds are particularly useful in making polyurethane compositions and/or polyisocyanurate polymers. The polyether polyol reacts with a polyisocyanate in the presence of a catalyst to prepare the polymers, particularly in foam form. When a polyisocyanurate foam is desired, the polyol-polyisocyanate polymerization is carried out by resort to an isocyanurate group formation catalyst which is used to trimerize the isocyanate groups to form the isocyanurate linkages.

The polyether polyols are generally prepared by the catalytic addition of an alkylene oxide or mixture of alkylene oxides, either simultaneously or sequentially to an organic compound usually having at least two active hydrogen atoms. The alkoxylation catalyst may be alkaline, neutral or acid, with an alkaline catalyst, such as an alkali metal hydroxide being most preferred. In a commerical operation, the usual catalysts are either sodium hydroxide or potassium hydroxide.

However, alkoxylation catalysts of this type have a number of drawbacks. Paramount among these is the requirement that the base employed after the alkoxylation reaction is completed be neutralized. The resultant salt must then be filtered from the polyol. This filtration step, of course, adds considerable cost and time to the overall process.

It would, therefore, be an advantage in the art if a catalyst were found which would overcome the just mentioned deficiency. It would be a further advantage if such portion of the catalyst which remains unused after the alkoxylation reaction could somehow be of further use in preparing polymer products which employ such polyether polyols.

Therefore, it becomes a principal object of the present invention to provide a method of making polyether polyols useful in preparing polyisocyanurate polymers, which polyether polyol method avoids the just discussed prior art drawback of employing conventional catalysts such as potassium hydroxide or sodium hydroxide. Other objects will appear hereinafter.

SUMMARY OF THE INVENTION

It has been found that the disadvantages of employing an alkali metal base catalyst normally used in preparing polyether polyols may be overcome by employing in said oxyalkylation process a catalyst selected from the group consisting of carbamate salts, aminophenols, hexahydro-s-tiazines and tetrahydrooxadiazines. Use of such catalysts not only aids in effecting oxyalkylation of an alcohol initiator but, in addition, the so-produced polyether polyol then may be used as such in making polyisocyanurate polymers without further addition of catalysts of this type normally used to promote the trimerization of isocyanate groups to form isocyanurate linkages since the just-mentioned group of catalysts are known polyisocyanurate catalysts. As a minimum advantage the amount of polyisocyanurate catalyst required is reduced due to its being already present in the polyether polyol source.

DETAILED DESCRIPTION OF THE INVENTION

The method of the invention basically follows prior art modes of making polyether polyols by oxyalkylating an alcohol through the catalytic addition of an alkylene oxide to said alcohol in presence of an oxyalkylating catalyst. The improvement here which is the gist of the invention includes utilizing as said oxyalkylating catalyst, a catalyst of the type mentioned above normally used to promote the trimerization of isocyanate groups to form isocyanurate linkages. Such catalyst of this type used in making polyisocyanurate polymers now has surprisingly been found here to be also useful in a conventional oxyalkylation reaction.

A number of benefits thus result from use of such isocyanurate catalyst in place of a conventional oxyalkylation catalyst such as an alkali metal hydroxide catalyst. Since the isocyanurate catalyst is soluble in the polyol produced, and no neutralization is necessary, no subsequent filtration step is thus required. In addition, the final polyether polyol contains, of course, the isocyanurate catalyst used to promote the oxyalkylation reaction, and therefore, when subsequently employed to form a polyisocyanurate elastomer or foam requires addition of only small amounts of additional catalyst. In some cases, no further catalyst addition is required.

As noted above, preparation of a polyether polyol is well known in the art as evidenced, for example, by U.S. Pat. Nos. 3,988,302; 3,190,927; 3,346,557 and other. The polyether polyols as prepared in the present invention are made by the catalytic addition through use of the particular catalysts mentioned here of an alkylene oxide or mixture of alkylene oxides, either simultaneously or sequentially to an organic compound having two or three active hydrogen atoms. Representative compounds of this type include polyhydric alcohols, such as ethylene glycol, propylene glycol, isomeric butylene glycols, 1,5-pentane diol, 1,6-hexane diol, glycerol, trimethylolpropane, 1,2,6-hexane triol, diethylene glycol, dipropylene glycol, 1,1-trimethylolethane, ethanolamine, diethanolamine, 2,(2-aminoethyl) ethanol, etc.

Alkylene oxides which may be employed in the preparation of the polyether polyols through the process of the present invention include ethylene oxide, propylene oxide, the isomeric normal butylene oxides, hexylene oxide, octylene oxide, dodecene oxide, methoxy and other alkoxy propylene oxides, styrene oxide and cyclohexene oxide. Halogenated alkylene oxides may also be used, such as epichlorohydrin, epiiodohydrin, epibromohydrin, 3,3-dichloropropylene oxide, 3-chloro-1,2-epoxypropane, 3-chloro-1,2-epoxybutane, 1-chloro-2,3-epoxybutane, 3,4-dichloro-1,2-epoxybutane, 1,4-dichloro-2,3-epoxybutane, 1-chloro-2,3-epoxybutane, and 3,3,3-trichloropropylene oxide. Mixtures of any of the above alkylene oxides may also be employed. Likewise, the polyether polyols can contain random addition, block addition or random and block addition. Preferred oxides are ehtylene and propylene oxide or mixtures.

The amount of alkylene oxide added to the alcohol initiator may range over a wide range of about 1-100 moles of alkylene oxide per mole of initiator. More often, 1-50 moles of alkylene oxide are reacted per mole of initiator.

The temperature of reaction may range from about 50° C. to about 200° C., and more often is 50°-150° C.

Usually the polyether polyol produced by the method of the invention has a hydroxyl number of 50-1,000. The hydroxyl number is defined as the number of milligrams of potassium hydroxide required for the complete neutralization of the hydrolysis product of the full acetylated derivative prepared from one gram of polyol.

When a volatile alkylene oxide is employed, the reactions are normally conducted in a closed vessel at ambient pressure at the particular temperature employed. Thus, the reaction pressure here may range from atmospheric pressure up to a pressure of about 1,000 psig.

The amount of catalyst utilized may vary over a wide weight percentage range based on the weight of the alcohol reactant. Usually an amount of catalyst ranging from about 0.01 to about 5 weight percent is employed, based on the weight of the alcohol reactant. More often, the amount employed is 0.1-2%, and most often is 0.3-1%.

The resultant polyether polyols then are used in a conventional manner in order to prepare isocyanurate foams and other types of isocyanurate polymers. Such polyisocyanurates may be made using the polyols of the invention according to methods of preparation described in U.S. Pat. Nos. 4,026,836; 3,745,133; and 3,644,232, to name a few.

The invention will be illustrated further with respect to the following specific examples, which are given by way of illustration and not as limitations on the scope of this invention.

EXAMPLE 1

A five gallon kettle was charged with 10 lbs. of trimethylolpropane and then heated to 130° C. It was held at 130° C. for ½ hour while being purged with nitrogen. The reaction was then cooled to 90° C. and 44.3 grams of DMP-30 [2,4,6-tri(dimethylaminomethyl)phenol, sold by Rohm and Haas Company] was added, followed by reheating the reaction mass to 130° C. Over a ½ hour period, 9.5 lbs. of ethylene oxide was added, followed by digestion for 1 hour at this temperature. The reaction mass was cooled to 90° C. and 8.7 grams of 2,6-di-tert-butyl-p-cresol was added. It was then stripped at 100° C. and 100 mm Hq vacuum for 15 minutes and discharged.

The polyol had a hydroxyl number of 646, pH of 12.70, and contained 0.069 meq. amine per gram of polyol.

EXAMPLE 2

In accordance with Example 1, a 5 gallon kettle was charged with 5 lbs. of trimethylolpropane and heated to 130° C. It was held at 130° C. while purging with nitrogen for ½ hour and then cooled to 90° C. 44 grams of POLYCAT 41 [1,3,5 tris-(N,N dimethylaminopropyl) hexahydro-s-triazine sold by Abbott Laboratories] was added and the reaction mass reheated to 110° C. 4.75 lbs. of ethylene oxide was added over a 25 minute period followed by digesting at 110° C. for 1 hour.

The reaction mass was then cooled at 80° C. and placed under 80 mm Hg vaccuum for ½ hour and then discharged.

The polyol had an OH# of 631, pH of 13.3 and a total amine content of 0.152 meq. amine per gram polyol.

EXAMPLE 3

Here a 5 gallon kettle was charged with 2 lbs. of glycerin and 10 grams of 1-2(hydroxyethyl)-3,5 bis(N, N-dimethylaminopropyl) hexadydro-s-triazine. This was heated to 120° C. and 4.3 lbs. of ethylene oxide added. The reaction mass was digested for 1½ hours at 120° C., vented and discharged. The polyol had a OH# of 569, pH of 12.95, and total amine of 0.049 meq./gram.

EXAMPLE 4

To a 1500 ml kettle was charged 500 grams of trimethylolpropane and 10 grams of 3,5-bis(N,N'-dimethylaminopropyl)-1, 3, 5-tetrahydrooxadiazine (I). The mixture was heated to 90° C. then 475 grams of ethylene oxide was added over a 1-hour long period. The reaction was heated to 110° C. and digested for 1½ hours. It was then stripped at 80 mm Hg vac and 110° C. for 30 minutes. The product had an hydroxyl number of 652.

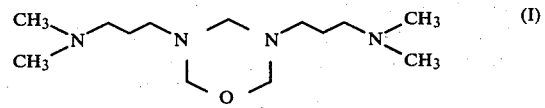

EXAMPLE 5

The following foams were prepared by premixing the B-component, then adding the isocyanurate catalyst and rapidly mixing. The reaction was then poured into an open mold and allowed to rise.

TABLE 1

| B-Component | A | B | C |
| --- | --- | --- | --- |
| polyol example I | 10.15 | — | — |
| polyol example II | — | 10.15 | — |
| polyol example III | — | — | 11.1 |
| M & T'S T-45[1] | 1.0 | 1.0 | 1.0 |
| POLYCAT 41[2] | 0.5 | 0.5 | 0.5 |
| DC-193[3] | 0.5 | 0.5 | 0.5 |
| F11B (fluorocarbon) | 12 | 12 | 12 |
| MONDUR MR[4] | 75.4 | 75.0 | 74.6 |
| cream time(sec) | 4 | 4 | 6 |
| tack free time(sec) | 15 | 60 | 15 |
| rise time(sec) | 25 | 60 | 30 |

[1]50% potassium octoate in a glycol solvent.
[2]A product of Abbott Laboratories, 1,3,5 tris-(N,N-dimethylaminopropyl) hexahydro-s-triazine.
[3]Product of Dow Corning, a silicone.
[4]A polyisocyanate product of Mobay Chemical Co., 2.7 functionality made by phosgenating the reaction product of aniline and formaldehyde.

Although the invention has been described in considerable detail in the foregoing disclosure, it is to be understood that such details are solely for the purpose of illustration and that many variations can be made by those skilled in the art without departing from the spirit and scope of the invention except as set forth in the claims.

We claim:

1. A method of preparing a polyether polyol useful in making a polyisocyanurate polymer, which comprises the steps of oxyalkylating an alcohol having a functionality of two or three by the catalytic addition of an alkylene oxide to said alcohol in presence of an oxyalkylating catalyst selected from the group consisting of aminophenols, hexahydro-s-triazines and tetrahydrooxadiazines.

2. The method of claim 1 wherein said oxyalkylating is carried out at a temperature of 50–200° C.

3. The method of claim 1 wherein said oxyalkylating catalyst is 2,4,6-tris(dimethylaminomethyl)phenol.

4. The method of claim 1 wherein said oxyalkylating catalyst is 1,3,5-tris(N,N-dimethylaminopropyl) hexahydro-s-triazine.

5. The method of claim 1 wherein said oxyalkylating catalyst is 1-(2-hydroxyethyl)-3,5,-bis(N,N-dimethylaminopropyl) hexahydro-s-triazine.

6. The method of claim 1 wherein said oxyalkylating agent is ethylene oxide.

7. The method of claim 1 wherein said oxyalkylating agent is propylene oxide.

8. The method of claim 1 wherein said oxyalkylating agent is a mixture of propylene oxide and ethylene oxide.

9. The method of claim 1 wherein said catalyst is employed in an amount ranging from about 0.1% to about 2% based on the weight of the alcohol reactant.

10. The method of claim 9 wherein said catalyst amount is 0.3–1%.

* * * * *